United States Patent
Doerr et al.

(10) Patent No.: US 9,770,586 B2
(45) Date of Patent: Sep. 26, 2017

(54) IMPLANT WITH FIXING DEVICE AND INSERTION APPARATUS FOR IMPLANT

(71) Applicant: Biotronik SE & Co. KG, Berlin (DE)

(72) Inventors: Thomas Doerr, Berlin (DE); Michael Diebold, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 0 days.

(21) Appl. No.: 14/802,951

(22) Filed: Jul. 17, 2015

(65) Prior Publication Data

US 2016/0051810 A1 Feb. 25, 2016

Related U.S. Application Data

(60) Provisional application No. 62/038,840, filed on Aug. 19, 2014.

(51) Int. Cl.
| A61N 1/05 | (2006.01) |
|---|---|
| A61N 1/375 | (2006.01) |
| A61N 1/372 | (2006.01) |

(52) U.S. Cl.
CPC ........... *A61N 1/059* (2013.01); *A61N 1/0587* (2013.01); *A61N 1/372* (2013.01); *A61N 1/375* (2013.01); *A61N 1/057* (2013.01); *A61N 1/3756* (2013.01); *A61N 2001/058* (2013.01)

(58) Field of Classification Search
CPC ...... A61N 1/057; A61N 1/0587; A61N 1/059; A61N 1/372; A61N 1/375; A61N 1/3756; A61N 1/0573; A61N 2001/058; A61B 17/3468
USPC ...................................... 607/9, 119
See application file for complete search history.

(56) References Cited

U.S. PATENT DOCUMENTS

| 4,157,720 A * | 6/1979 | Greatbatch | A61N 1/375 607/131 |
|---|---|---|---|
| 4,280,513 A * | 7/1981 | Gilbert | A61N 1/0587 607/119 |
| 2002/0177888 A1* | 11/2002 | Williams | A61N 1/056 607/122 |
| 2003/0204191 A1* | 10/2003 | Sater | A61B 17/0483 606/104 |
| 2004/0015193 A1* | 1/2004 | Lamson | A61N 1/056 607/9 |
| 2005/0004644 A1 | 1/2005 | Kelsch et al. | |

(Continued)

FOREIGN PATENT DOCUMENTS

| DE | 2840307 A1 | 3/1979 |
|---|---|---|
| WO | 2013098644 A2 | 7/2013 |

OTHER PUBLICATIONS

European Search Report received from EP Application Serial No. 15167604, dated Jan. 5, 2016, 5 pages.

*Primary Examiner* — Michael Carey
*Assistant Examiner* — Pamela M Bays
(74) *Attorney, Agent, or Firm* — Arc IP Law, PC; Joseph J. Mayo (57) ABSTRACT

Embodiments include a medical implant including a fixing device with at least one fixing element to fix the implant at a site of implantation. The implant includes a belt drive that rotates an actuation device, wherein the actuation device is coupled to the fixing device and converts the rotary movement into a longitudinal movement of the fixing device. Embodiments include an insertion device to insert the medical implant.

15 Claims, 6 Drawing Sheets

(56) References Cited

U.S. PATENT DOCUMENTS

2006/0195093 A1* 8/2006 Jahng ................ A61B 17/3421
606/254
2011/0106145 A1 5/2011 Jeong
2011/0238077 A1 9/2011 Wenger
2012/0330392 A1 12/2012 Regnier et al.

* cited by examiner

IMPLANT WITH FIXING DEVICE AND INSERTION APPARATUS FOR IMPLANT

This application claims the benefit of U.S. Provisional Patent Application 62/038,840 filed on 19 Aug. 2014, the specification of which is hereby incorporated herein by reference.

BACKGROUND OF THE INVENTION

Field of the Invention

Embodiments of the invention generally relate to an implant with a fixing device that may be inserted into a human or animal body, and to an insertion apparatus including the implant.

Description of the Related Art

Generally, implants, for example endocardial and epicardial electrodes, are inserted into the human or animal body, and such implants are typically fixed using what is known as a fixing helix. Typically, the fixing helix is screwed in either by turning the entire implant or by unscrewing the fixing helix using a Cardan drive within an electrode line of the implant.

This procedure, however, is generally only suitable to a limited extent for implantation in narrow regions and regions that are difficult to access, such as the myocardium, if no direct access to the site of implantation is possible.

BRIEF SUMMARY OF THE INVENTION

One or more embodiments of the invention provide a securely fixable implant to implant in narrow sites of implantation or sites of implantation that are difficult to access.

At least one embodiment of the invention provides an insertion apparatus for such an implant.

One or more embodiments of the invention are achieved in accordance with elements of the independent claims presented herein. Embodiments of the invention will emerge from the other claims, the description and the drawings presented herein.

At least one embodiment of the invention includes a medical implant with a fixing device that includes at least one fixing element to fix the implant at a site of implantation. In one or more embodiments, the implant may include a belt drive that rotates an actuation device, wherein the actuation device is coupled to the fixing device. In at least one embodiment, the actuation device may convert rotary movement from the belt drive into a longitudinal movement of the fixing device.

In one or more embodiments of the invention, the implant may include a fixing element, such as a fixing helix, that may be implanted in very narrow tissue gaps and may be securely screwed into the tissue to be implanted. In at least one embodiment, an exact number of revolutions to unscrew the fixing helix may be guaranteed.

One or more embodiments may include a tear-resistant, sufficiently thin, thread that may be easily guided in an insertion apparatus as a belt of the belt drive.

In at least one embodiment, a fixing helix may be unscrewed from an implant that may be slid flat under the pericardium or from a comparable implant. For example, one or more embodiments may include a thread wound around the fixing helix or the implant, such that the thread may rotate as the fixing helix or the implant is pulled and may then detach from the implant as necessary when the fixing helix is completely unscrewed. At least one embodiment of the invention may include simultaneous unscrewing of two fixing helices in an opposite direction of rotation, such that the implant cannot loosen on its own, but is securely anchored at the site of implantation.

In one or more embodiments, the medical implant may be used in the form of, or may include, an epicardial or endocardial pulse generator or a neurostimulator.

In at least one embodiment of the invention, the belt drive may include a belt that may loop around the actuation device, for example a number of times with a defined number of windings, wherein the actuation device may include a rotationally symmetrical contact face for the belt of the belt drive. By fixing the belt on the contact face, in one or more embodiments, the actuation device may be rotated.

In at least one embodiment of the invention, the belt of the belt drive may be arranged detachably on the actuation device, such that the belt is decoupled or detached in terms of drive from the actuation device when a predefined number of revolutions of the actuation device are reached. As such, in one or more embodiments, a defined number of revolutions of the actuation device may be reached, which in turn may specify a defined advance movement of the fixing element and therefore a defined projection of the fixing element beyond the implant housing. As such, in at least one embodiment, a defined depth may be achieved, wherein the fixing element digs into the tissue at the site of implantation.

In at least one embodiment of the invention, the belt drive may move the actuation device in both directions of rotation. One or more embodiments may include two belt parts fastened to the actuation device such that two free ends of the belt extend away from the actuation device. In at least one embodiment, if one end is pulled, the actuation device rotates in one direction; and if the other end is pulled, the actuation device rotates in the opposite direction.

In at least one embodiment, the fixing device may include a plurality of fixing elements. In one or more embodiments, the plurality of fixing elements may be moved simultaneously when the actuation device rotates. As such, in at least one embodiment, a particularly reliable anchoring of the implant at the site of implantation may be produced.

In one or more embodiments, the plurality of fixing elements may be displaceable and/or tiltable relative to one another at least in the extended state, such that they are arranged to be flexible relative to one another. In at least one embodiment, if the plurality of fixing elements may be arranged to be flexible relative to one another when used as intended, the plurality of fixing elements may compensate for a relative movement produced by a moving tissue, for example at a myocardium.

At least one embodiment of the invention may include a locking mechanism, wherein the fixing device may be coupled to the locking mechanism, which at least prevents a longitudinal movement when the belt drive is detached or decoupled. In one or more embodiments, the locking mechanism may then always prevent a further rotation of the fixing helix when the belt is fully extracted, for example in the manner of a retaining pawl, which is initially blocked by the belt.

In at least one embodiment, the belt or the belts of the belt drive may be coupled in a form-fitting manner to the actuation device. In one or more embodiments, the belt or the belts and the actuation device may include structures that engage with one another, which cooperate with one another as the actuation device rotates. In at least one embodiment, the belt may include mechanical contour elements in specific regions, which may produce a coupling with the actuation device only in a defined region, for example in the form of small balls or nubs, which may engage in indentations in the contact face between the actuation device and the belt. As such, in one or more embodiments, the contact between the actuation device and the belt may be improved and may cause a selective introduction of force to rotate the actuation device.

In at least one embodiment, the belt may be formed from, or include, resorbable material. As such, in one or more embodiments, the belt may remain on the implant without causing a problem.

By way of at least one embodiment, the fixing device may include one or more fixing helices. In one or more embodiments, the one or more fixing helices may move particularly easily via a rotational movement in a direction of advancement.

At least one embodiment of the invention may include an insertion device for a medical implant, wherein the medical implant includes a fixing device with at least one fixing element to fix the implant at a site of implantation. In one or more embodiments, the implant may include a belt drive, which rotates an actuation device, wherein the actuation device is coupled to the fixing device. In at least one embodiment, the actuation device may convert the rotary movement of the belt drive into a longitudinal movement of the fixing device.

According to one or more embodiments of the invention, the insertion device may include an implantation tool and a receptacle, wherein a belt drive may be actuated via the insertion apparatus. In at least one embodiment, the belt drive is part of the implantation tool, such that the implant including the fixing device is initially completely received, and, upon actuation of the mechanism, the belt drive removes the implant and the fixing device in equal measure from the implantation tool and drives the implant and the fixing device into the tissue. In the case of a fixing helix, according to at least one embodiment, the fixing helix is unscrewed in equal measure from the implantation tool and is screwed into the tissue.

BRIEF DESCRIPTION OF THE DRAWINGS

The above and other aspects, features and advantages of at least one embodiment of the invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1A:
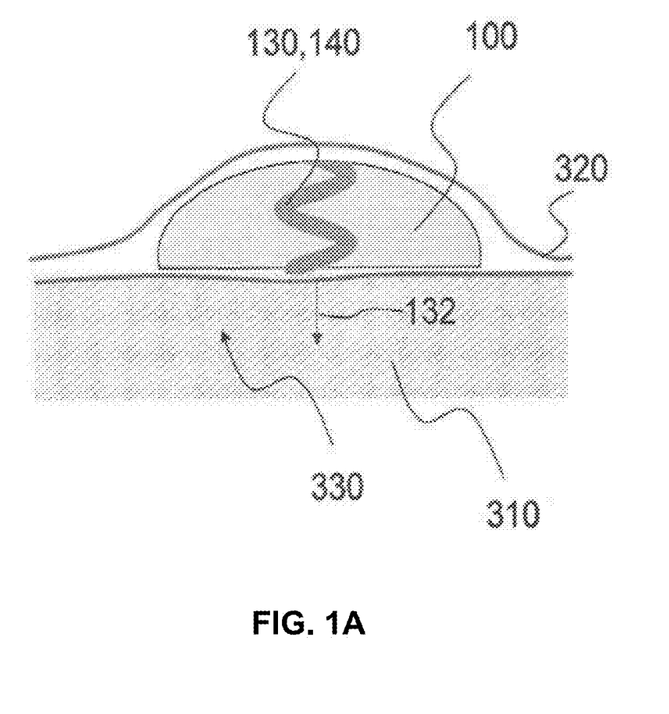
FIG. 1A schematically shows a sectional view an implant including a fixing helix prior to fixing of the implant.
Figure 1B:
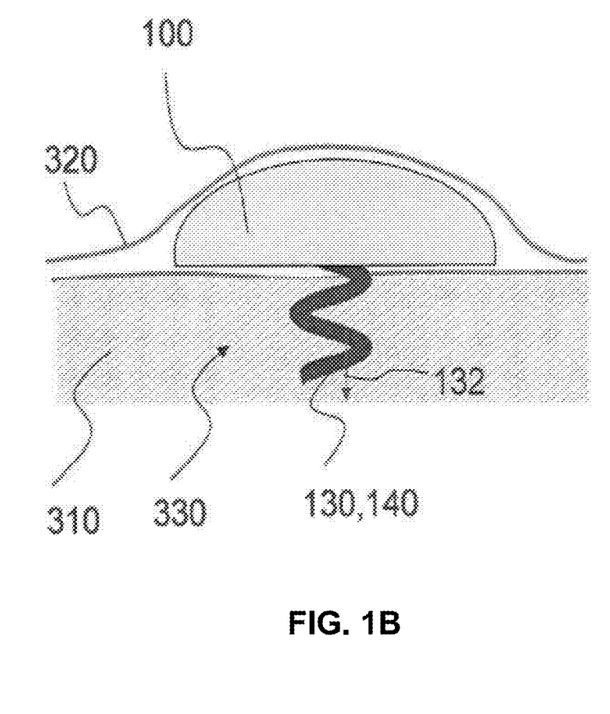
FIG. 1B schematically shows a sectional view an implant including a fixing helix after fixing of the implant.

According to one or more embodiments of the invention, FIGS. 1A and 1B show, as sectional views, an implant 100 including a fixing element 140, formed as a fixing helix, of a fixing device 130 prior to the fixing of the implant (FIG. 1A) and after the fixing of the implant (FIG. 1B) in a site of implantation 330. As shown in FIG. 1A, in at least one embodiment of the invention, the implant 100 may be formed as or may include, for example, an epicardial pulse generator, which is initially positioned using an insertion apparatus (not illustrated) between the myocardium 310 and pericardium 320. As shown in FIG. 1B, in at least one embodiment, the implant 100 may then be fixed in the tissue of the myocardium 310 of the site of implantation 330 using a fixing element 140 formed as, or including, a fixing helix, which may be unscrewed from the implant 100 in a longitudinal direction 132, as shown in FIG. 1A.

Figure 2A:
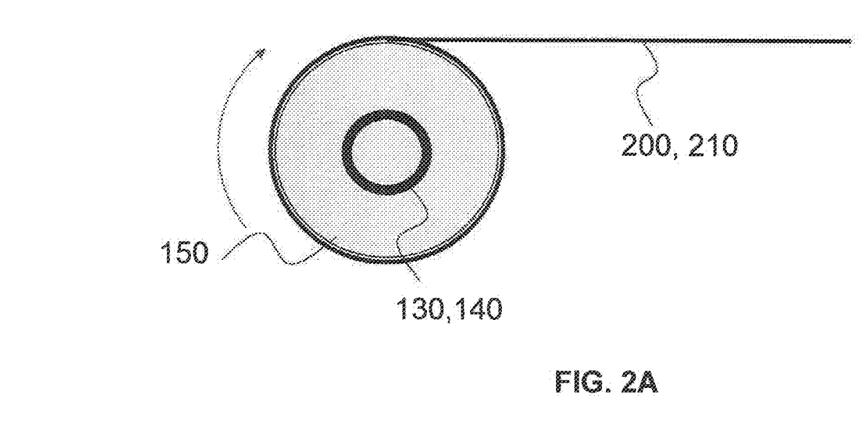
FIG. 2A schematically shows a plan view of an underside of an implant in accordance with an embodiment of the invention.
Figure 2B:
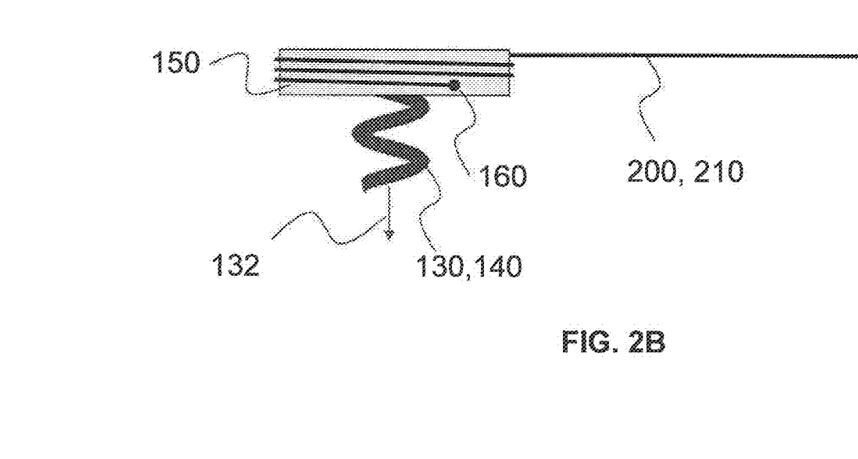
FIG. 2B schematically shows a plan view of a side view of an implant in accordance with an embodiment of the invention.

As shown in FIGS. 2A and 2B, in side view, in at least one embodiment, the implant 100 may include a belt drive 200, which rotates an actuation device 150, wherein the actuation device 150 is coupled to the fixing device 130. In one or more embodiments, the actuation device 150 may convert the rotary movement of the belt drive 200 into a longitudinal movement of the fixing device 130. According to at least one embodiment, with a fixing helix as fixing element 140, which may include a thread with a given pitch, the longitudinal movement is coupled with a rotation of the fixing helix in accordance with the pitch of the thread of the fixing helix. In one or more embodiments, the actuation device 150 may be fitted in the implant be longitudinally displaceable along an axis, such that the fixing helix moves the actuation device 150 over the axis as it is screwed into the bodily tissue. In at least one embodiment, the actuation device 150 may be fitted in the implant such that the axis is formed with a thread of corresponding pitch, which actively performs the longitudinal displacement of the actuation device.

In one or more embodiments, the belt drive 200 may loop around a rotationally symmetrical contact face of the actuation device 150 via a thread-like belt 210. In at least one embodiment, the number of windings may determine the maximum possible deflection of the fixing element 140 in the longitudinal direction 132, denoted in FIGS. 2A and 2B by an arrow. In one or more embodiments, the belt 210 may be fixed on the contact face at a point 160. In at least one embodiment, the actuation device 150 may be rotatably mounted (not illustrated). By way of one or more embodiments, if the free end of the belt 210 is pulled, the actuation device 150 rotates, and the fixing element 140 may cooperate with a mating thread, or the like, and may be moved in the longitudinal direction 132.

According to at least one embodiment, the belt 210 of the belt drive 200 may be arranged detachably on the actuation device 150, such that the belt 210 detaches from the actuation device 150 when a predefined number of revolutions of the actuation device 150 is reached, or the belt detaches when the fixing element 140 is fully unscrewed. In one or more embodiments, the belt 210 may be formed from, or include, resorbable material and may remain in the tissue.

Figure 3:
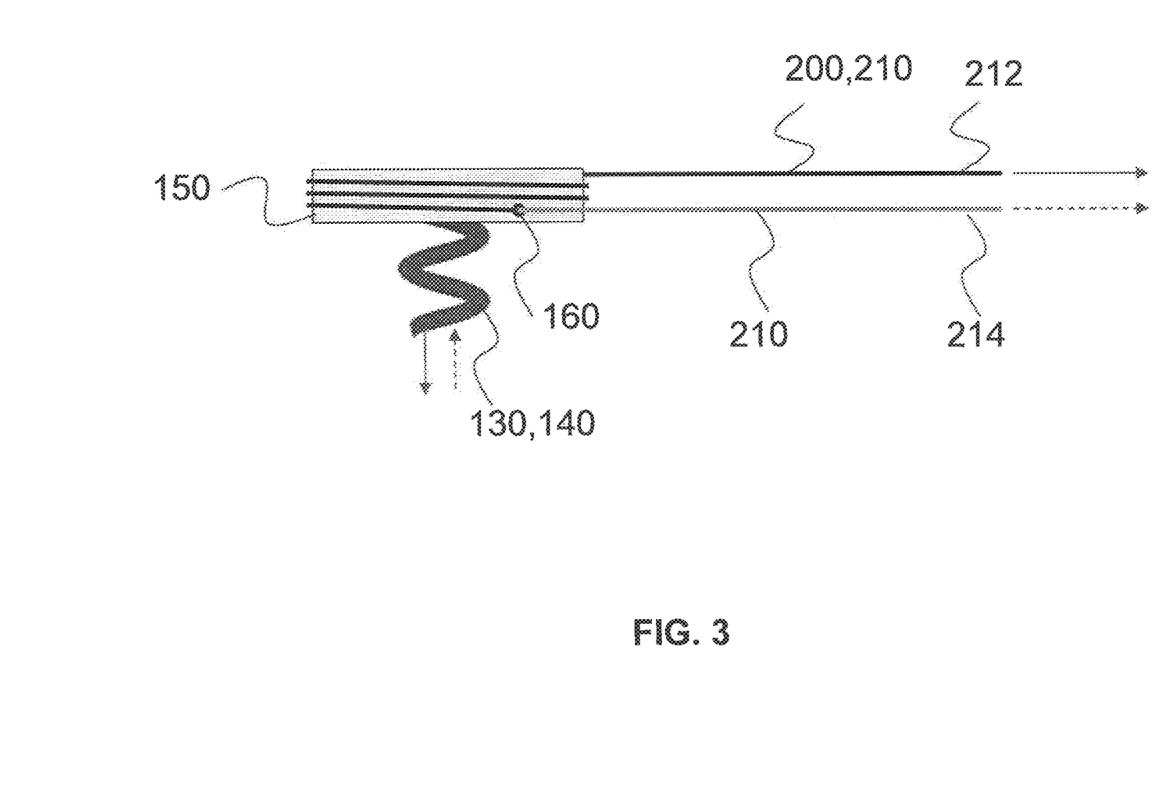
FIG. 3 schematically shows a side view of an implant including a fixing helix in accordance with an embodiment of the invention.

FIG. 3 shows a variant of the arrangements shown in FIGS. 2A and 2B, according to one or more embodiments. As shown in FIG. 3, in at least one embodiment, the belt 210 may be attached such that two belt ends 212, 214 extend away from the actuation device 150. Depending on which of the ends 212, 214 are tensioned, by way of one or more embodiments, the actuation device 150 may turn in one direction of rotation or the other. As such, in at least one embodiment, the actuation device 150 may be moved in both directions of rotation, such that the fixing helix may be screwed into the tissue by pulling on the belt end 212 and unscrewed by pulling on the other belt end 214.

In one or more embodiments, the belt 210 may be fixed at a point 160 such that the belt 210 may detach from the actuation device 150 when the fixing element 140 is fully unscrewed and the first part of the belt 210 is extracted.

In at least one embodiment of the invention, the belt 210 may be fastened such that the belt 210 decouples from the actuation device 150 when the necessary number of revolutions of screwing into the tissue have been made, and may decouple again when the mechanism of unscrewing is actuated. In one or more embodiments, once the fixing element has been screwed in, the entire thread-like belt 210 is detached, such that the entire belt 210 is fully extracted.

Figure 4:
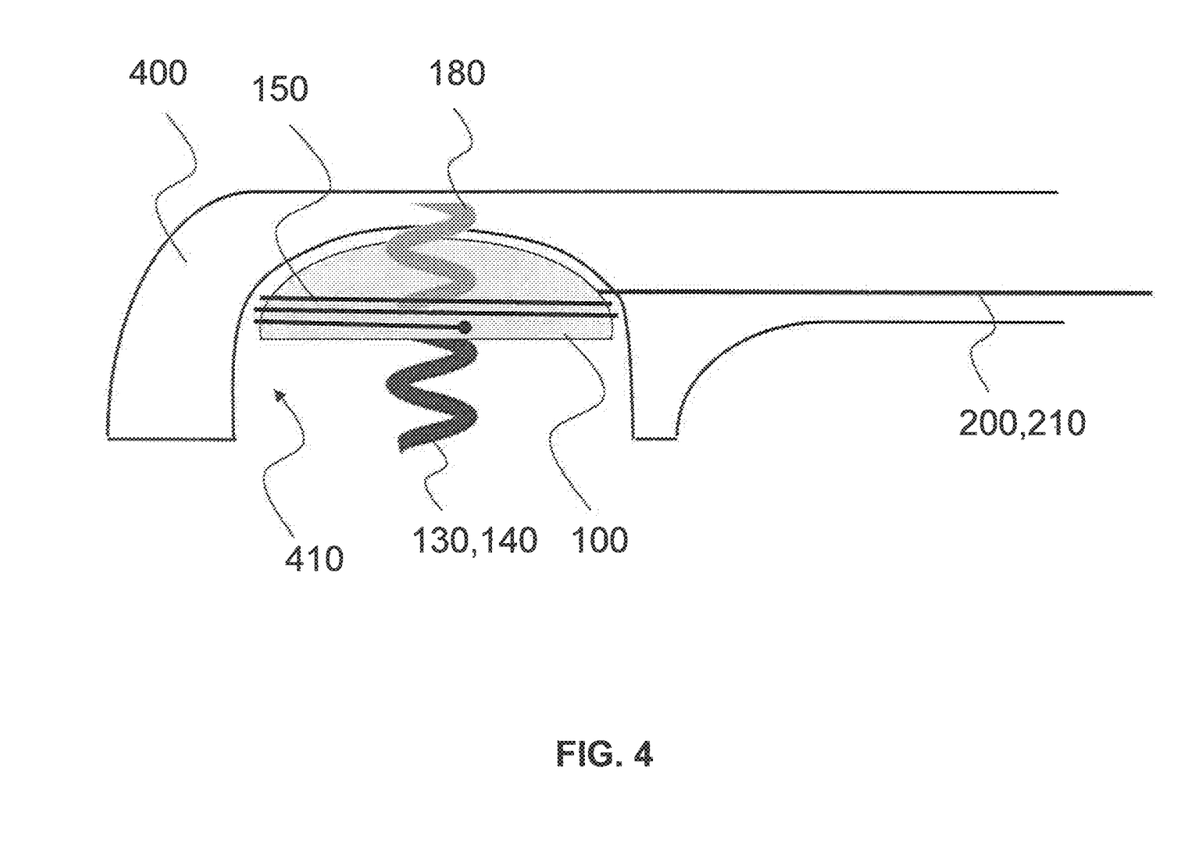
FIG. 4 schematically shows a side view of an insertion apparatus with an implant including a fixing helix with a partially cut-away mount in accordance with an embodiment of the invention.

FIG. 4 shows a side view of an insertion apparatus 400 including a medical implant 100 and a fixing device 130, with a partly cut-away mount, according to one or more embodiments of the invention. In at least one embodiment, the insertion device 400 may include a receptacle 410 that corresponds to the implant 100. In one or more embodiments, the fixing device 130 may include a fixing helix as fixing element 140.

By way of at least one embodiment, a belt drive 200 may be actuated via the insertion apparatus 400, wherein a thread-like belt 210 leads through the mount to the proximal end of the insertion apparatus 400. Since the implant 100 is received fully in the receptacle 410, according to one or more embodiments, the implant 100 may be introduced into a tissue gap without access being inhibited by the fixed fixing element 140, such as a fixing helix.

In at least one embodiment, when the belt 210 to the actuation device 150 is pulled, the entire rotationally symmetrical implant 100 may be rotated in the implantation tool 400. In one or more embodiments, the implantation tool 400 may include a helical guide 180 of the implant 100 with approximately identical pitch compared with that of the fixing element 140 on the implant 100, such that the implant 100 may be unscrewed from the insertion apparatus 400 and screwed it into the tissue at the same time.

By way of at least one embodiment, the force required to screw into the tissue may be adjusted in a controlled manner by the different pitch of both helices 180 and 140 in accordance with the target tissue.

One or more embodiments of the invention may include a mechanism to unscrew the implant 100 in a manner similar to the descriptions above.

Figure 5:
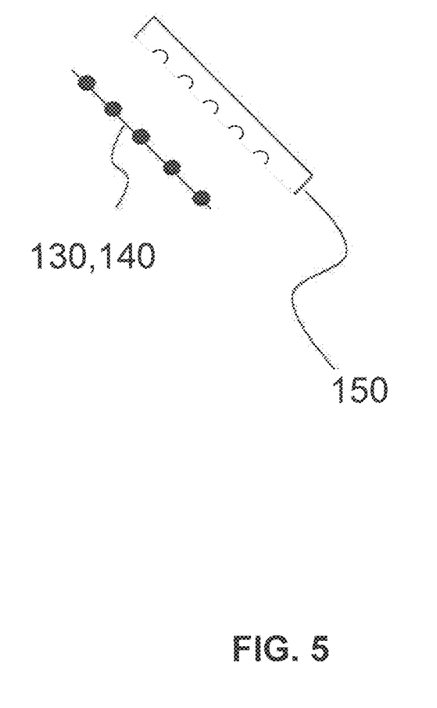
FIG. 5 schematically shows a belt drive in accordance with an embodiment of the invention.

FIG. 5 shows a belt drive 200 according to one or more embodiments of the invention. As shown in FIG. 5, in at least one embodiment, the belt 210 of the belt drive 200 may be coupled in a form-fitting manner to the actuation device 150. In one or more embodiments, the belt 210 and the actuation device 150 may include structures that engage with one another, which cooperate with one another as the actuation device 150 is rotated.

At least one embodiment of the invention fix an implant 100 securely and easily using a fixing element 140, such as a fixing helix, even at positions that are difficult to access.

Figure 6:
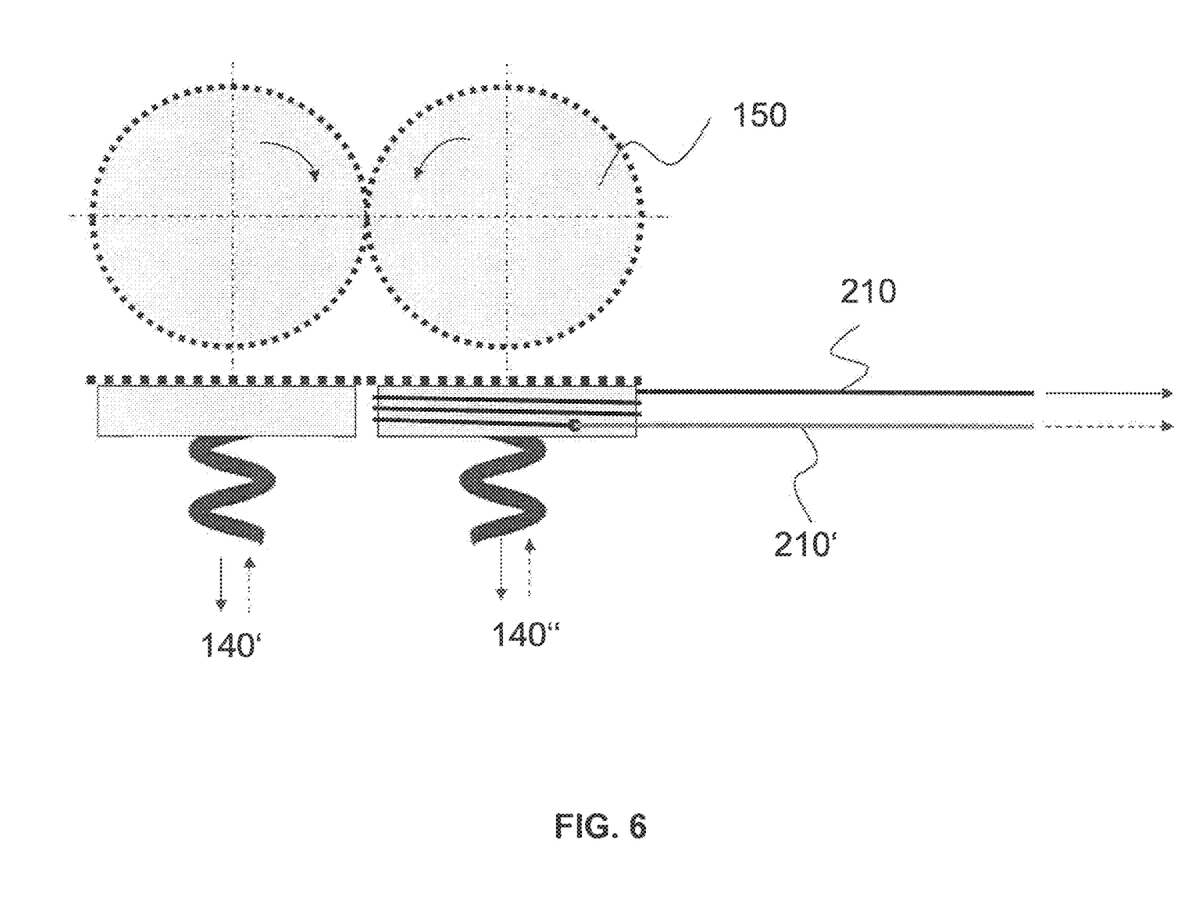
FIG. 6 schematically shows a side view of an implant in accordance with an embodiment of the invention.

FIG. 6 shows an implant including two fixing elements 140' and 140", such as two helices, according to one or more embodiments of the invention. In at least one embodiment, the two fixing elements 140' and 140" may be moved by a belt 210, 210' via the actuation device 150. By way of at least one embodiment, the belt 210 may be used to anchor the helices in the tissue and the belt 210' may be used to unscrew the helices from the tissue. In one or more embodiments, as shown in FIG. 6, the fixing elements 140' and 140" may be formed by, or include, oppositely directed helices, and the actuation apparatus 150 may be formed or positioned such that the helices screw into the tissue in opposite directions. For example, in at least one embodiment, one helix may be screwed in a clockwise direction and the other helix in an anti-clockwise direction. As the helices are unscrewed, according to at least one embodiment, the helices may be unscrewed in opposite directions, for example one helix in an anti-clockwise direction and the other helix in a clockwise direction. As such, in one or more embodiments, the implant cannot unscrew from the tissue as a result of movements, in particular heart movements.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A medical implant comprising:
   a fixing device comprising at least one fixing element configured to fix the medical implant at a site of implantation, and,
   a belt drive that rotates an actuation device,
   wherein the actuation device is coupled to the fixing device,
   wherein the actuation device converts rotary movement from the belt drive into a longitudinal movement of the fixing device,
   wherein the belt drive comprises a belt detachably arranged on the actuation device, such that the belt is decoupled or detached in terms of drive from the actuation device when a predefined number of revolutions of the actuation device is reached,
   wherein the at least one fixing element comprises a plurality of fixing elements, and
   wherein the plurality of fixing elements are one or more of displaceable and tiltable with respect to one another at least in an extended state.

2. The medical implant as claimed in claim 1, wherein said belt loops around the actuation device, and wherein the actuation device comprises a rotationally symmetric contact face corresponding to the belt of the belt drive.

3. The medical implant as claimed in claim 1, wherein the belt drive is configured to move the actuation device in both directions of rotation.

4. The medical implant as claimed in claim 1, wherein the plurality of fixing elements are movable simultaneously when the actuation device rotates.

5. The medical implant as claimed in claim 1, further comprising a locking mechanism, wherein the fixing device is coupled to the locking mechanism, and wherein the locking mechanism at least prevents a longitudinal movement when the belt drive is detached.

6. The medical implant as claimed in claim 2, wherein the belt of the belt drive is coupled in a form-fitting manner to the actuation device.

7. The medical implant as claimed in claim 2, wherein the belt and the actuation device comprise structures that engage with one another, and wherein the structures cooperate with one another when the actuation device rotates.

8. The medical implant as claimed in claim 7, wherein the structures comprise mechanical contour elements comprising small balls or nubs that couple with the actuation device in a defined region and that engage in indentations of the contact face between the actuation device and the belt.

9. The medical implant as claimed in claim 2, wherein the belt is formed from resorbable material.

10. The medical implant as claimed in claim 1, wherein the at least one fixing element comprises one or more fixing helices.

11. The medical implant as claimed in claim 1, wherein the medical implant is an epicardial or endocardial pulse generator or a neurostimulator.

12. The medical implant as claimed in claim 1, wherein the plurality of fixing elements comprise helices, wherein said belt drive further comprises a second belt, wherein said belt is configured to anchor said helices in tissue at said site of implantation, and wherein said second belt is configured to unscrew said helices from said tissue.

13. An insertion device for a medical implant comprising:
a medical implant, wherein the medical implant comprises
a fixing device comprising at least one fixing element configured to fix the medical implant at a site of implantation; and,
a belt drive that rotates an actuation device,
wherein the belt drive is actuated via the insertion device,
wherein the actuation device is coupled to the fixing device,
wherein the actuation device converts rotary movement from the belt drive into a longitudinal movement of the fixing device, and
wherein the belt drive comprises a belt detachably arranged on the actuation device, such that the belt is decoupled or detached in terms of drive from the actuation device when a predefined number of revolutions of the actuation device is reached; and,
a receptacle;
wherein the at least one fixing element comprises a plurality of fixing elements, and
wherein the plurality of fixing elements are one or more of displaceable and tiltable with respect to one another at least in an extended state.

14. A medical implant comprising:
a fixing device comprising at least one fixing element configured to fix the medical implant at a site of implantation, and,
a belt drive that rotates an actuation device,
wherein the actuation device is coupled to the fixing device,
wherein the actuation device converts rotary movement from the belt drive into a longitudinal movement of the fixing device,
wherein the belt drive comprises a belt detachably arranged on the actuation device, such that the belt is decoupled or detached in terms of drive from the actuation device when a predefined number of revolutions of the actuation device is reached,
wherein the at least one fixing element comprises a plurality of fixing elements, and
wherein the plurality of fixing elements comprise helices, wherein said belt drive further comprises a second belt, wherein said belt is configured to anchor said helices in tissue at said site of implantation, and wherein said second belt is configured to unscrew said helices from said tissue.

15. An insertion device for a medical implant comprising:
a medical implant, wherein the medical implant comprises
a fixing device comprising at least one fixing element configured to fix the medical implant at a site of implantation; and,
a belt drive that rotates an actuation device,
wherein the belt drive is actuated via the insertion device,
wherein the actuation device is coupled to the fixing device,
wherein the actuation device converts rotary movement from the belt drive into a longitudinal movement of the fixing device, and
wherein the belt drive comprises a belt detachably arranged on the actuation device, such that the belt is decoupled or detached in terms of drive from the actuation device when a predefined number of revolutions of the actuation device is reached; and,
a receptacle;
wherein the at least one fixing element comprises a plurality of fixing elements, and
wherein the plurality of fixing elements comprise helices, wherein said belt drive further comprises a second belt, wherein said belt is configured to anchor said helices in tissue at said site of implantation, and wherein said second belt is configured to unscrew said helices from said tissue.

* * * * *